United States Patent [19]

Fanning, Jr. et al.

[11] Patent Number: 5,120,877
[45] Date of Patent: Jun. 9, 1992

[54] PROCESS FOR THE PRODUCTION OF CARBONYL COMPOUNDS

[75] Inventors: Albert T. Fanning, Jr., Longview; Harry F. Goss, White Oak, both of Tex.

[73] Assignee: Eastman Kodak Company, Rochester, N.Y.

[21] Appl. No.: 644,148

[22] Filed: Jan. 22, 1991

[51] Int. Cl.$^5$ .................. C07C 45/30; C07B 41/00
[52] U.S. Cl. .................. 568/469.9; 568/398.8; 568/449; 568/475; 568/476
[58] Field of Search .............. 568/449, 469.9, 476, 568/475, 3

[56] References Cited

U.S. PATENT DOCUMENTS 1,697,265  1/1929  Ellis ................................ 568/469.9
4,448,892  5/1984  Kukes et al. ...................... 568/469.9

OTHER PUBLICATIONS

Ethylene and Its Industrial Derivatives, pp. 639-659, S. A. Miller, editor, Ernest Benn Limited, London, 1969. Abstract 74-83935V/48.

Primary Examiner—Warren B. Lone
Attorney, Agent, or Firm—Mark A. Montgomery; William P. Heath, Jr.

[57] ABSTRACT

A process for the production of carbonyl compounds such as acetaldehyde is provided. This process entails reacting alpha olefins with a catalyst system containing a noble metal oxidation catalyst, cupric ions, chloride ions, and a strong acid such as sulfuric acid followed by separating into a carbonyl compound stream and a reduced catalyst stream followed by oxidizing the catalyst stream and returning it to the reaction zone at a pH between about 0 and 2.

15 Claims, 3 Drawing Sheets

Wacker Oxidizer Simulation Without $H_2SO_4$

Wacker Oxidizer Simulation Without $H_2SO_4$

Wacker Oxidizer Simulation With $H_2SO_4$ (0.86%)

Sulfuric Acid Affect on Chlorination Under Wacker Oxidizer Conditions

PROCESS FOR THE PRODUCTION OF CARBONYL COMPOUNDS

FIELD OF THE INVENTION

The present invention relates to a process of producing carbonyl compounds. More particularly, the present invention relates to a process of producing carbonyl compounds by organic oxidation while retarding halogenation thus producing less halogenated byproducts.

BACKGROUND OF THE INVENTION

The production of carbonyl compounds by organic oxidation is well known. One well known process of producing carbonyl compounds by organic oxidation is the acetaldehyde Wacker Process. In this process, ethylene is oxidized to acetaldehyde in the presence of an aqueous copper chloride solution palladium catalyst. This process is disclosed by R. Jira in "Ethylene and It's Industrial Derivatives", Pages 639–659, S. A. Miller, editor, Ernest Benn Limited, London, 1969.

One consistent problem of the acetaldehyde Wacker process is the high production of chlorinated byproducts. The byproducts are derived from acetaldehyde, specifically chlorinated acetaldehyde (mono-, di-, and trichloroacetaldehyde) by oxychlorination of acetaldehyde with cupric chloride; chlorinated methanes from decarbonylation of chloroacetaldehydes or decarboxylation of chloroacetic acids; chlorocrotonaldehyde and chlorinated resins from condensation of acetaldehyde and monochloroacetaldehyde; and oxalic acid from repeated oxychlorination of acetaldehyde and hydrolysis of the products formed. These by-products plus acetic acid result in a significant ethylene yield loss. Chloride is also lost from the catalyst system through chlorination but can be made up by small incremental hydrochloric acid (HCl) addition to the catalyst.

Not only does the production of chlorinated byproducts reduce the product yield through ethylene loss but, from an environmental standpoint, the production of the chlorinated byproducts poses other significant problems since these chlorinated byproducts are hazardous materials and disposal is difficult and costly.

It would, therefore, be very desirable to be able to produce carbonyl compounds such as acetaldehyde at higher yield with reduced chlorination producing less halogenated byproducts.

SUMMARY OF THE INVENTION

The present invention is a process for the production of carbonyl compounds that produce low amounts of chlorinated byproducts and comprises:

(a) reacting an aqueous mixture of at least one alpha olefin, noble metal oxidation catalyst, cupric ions, chloride ions, and a strong acid selected from about 0.05 to 5 wt. % sulfuric acid, about 0.05 to 5 wt. % phosphoric acid, and about 1 to 5 wt. % hydrochloric acid in a reaction zone under conditions to produce carbonyl compounds;

(b) separating the mixture into a carbonyl compound stream, and a reduced catalyst stream;

(c) introducing an oxygen containing gas into said reduced catalyst stream under oxidation conditions; and (d) returning the catalyst stream to said reaction zone at a pH between about 0 and 2.

FIG. illustrates the amounts of the three chlorinated acetaldehydes that are produced over time in the reaction with the addition of strong acid.

Figure 3:
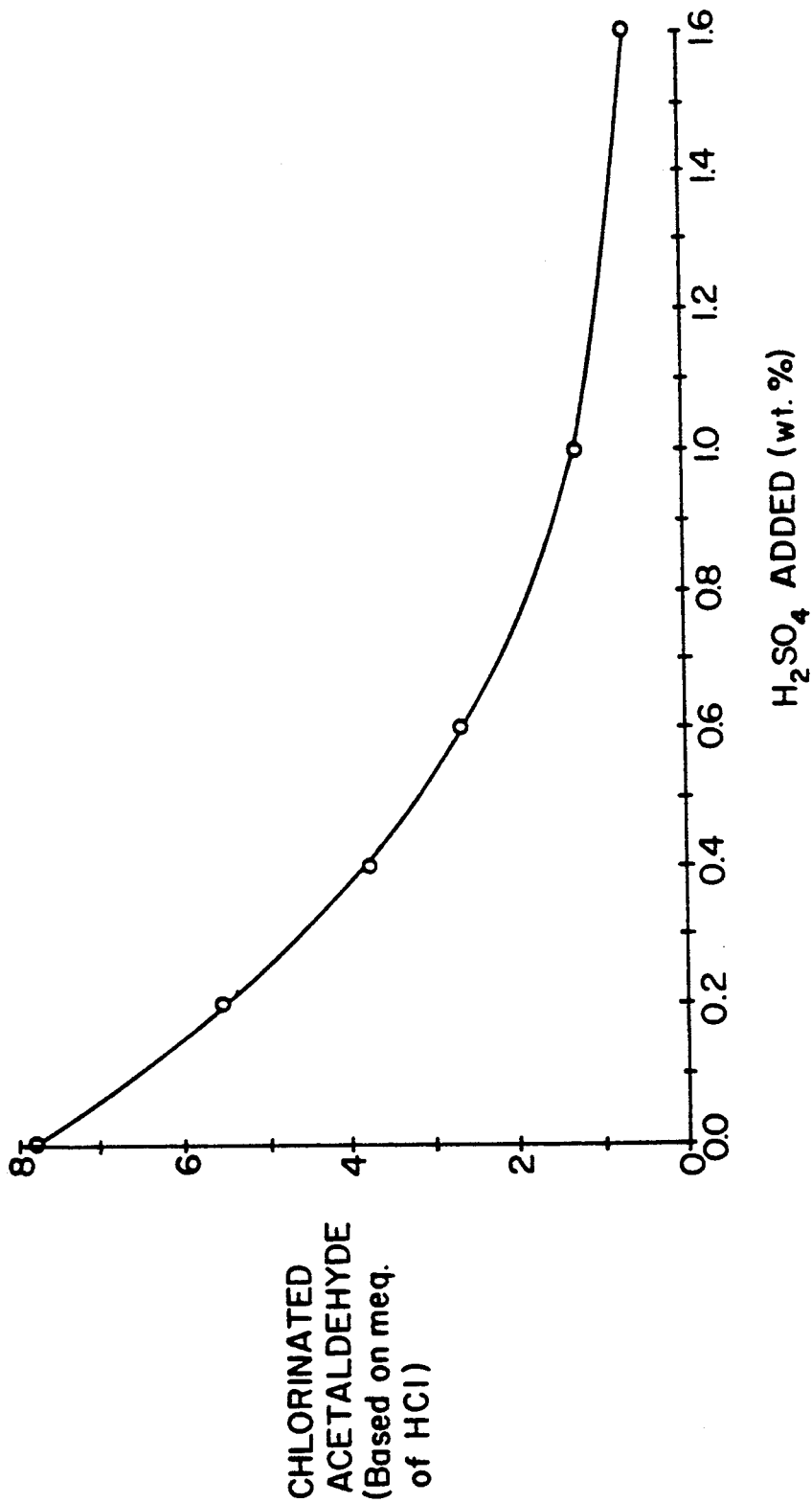

FIG. 3 illustrates the affect on chlorination at varying amounts of strong acid with the amount of chlorinated acetaldehyde expressed in milliequivalents of HC1.

DETAILED DESCRIPTION OF THE INVENTION

The process of the present invention produces carbonyl compounds at increased yield while significantly reducing the chlorinated byproducts such as the chloroacetaldehydes.

The process according to the present invention of producing carbonyl compounds while reducing the production of chlorinated byproducts preferably produces the carbonyl compounds from alpha olefins having 2 to 5 carbon atoms, more preferably from ethylene thereby producing acetaldehyde. The process of the present invention is a distinct improvement in the Wacker Process that produces acetaldehyde from ethylene by organic oxidation.

Suitable noble metal oxidation catalyst used in the reaction mixture in the process of the present invention can be selected from the group consisting of palladium, rhodium, ruthenium, iridium, platinum, gold and mercury with the salts of these metals being more preferred. The noble metal oxidation catalyst is preferably selected from the Group VIII noble metals and metal salts thereof with palladium salt being more preferred and palladium chloride being most preferred.

The reaction mixture in the process of the present invention also must contain cupric ions and chloride ions. The reaction mixture preferably contains between about 3 and 20 millimoles per liter of palladium chloride, between about 100 and 3,000 moles per liter of cupric chloride, and between about 10 and 1,000 millimoles cuprous chloride. More preferably the reaction mixture of Step (a) in the inventive process contains about 10 millimoles per liter palladium chloride, about 1,000 millimoles per liter cupric chloride, and about 300 millimoles per liter cuprous chloride.

The reaction mixture of Step (a) also contains a strong acid selected from 0.05 to 5 wt. % sulfuric acid, 0.05 to 5 weight percent phosphoric acid, and 1 to 5 weight percent hydrochloric acid with sulfuric acid being most preferred. The amount of sulfuric acid used in the reaction mixture is preferably between about 0.1 and 3 weight percent sulfuric acid with between about 0.1 and 2 weight percent sulfuric acid being most preferred.

The strong acid is preferably added to the Wacker catalyst mixture or a small portion of this mixture as makeup catalyst prior to being introduced into the continuous process such as in the reaction zone of Step (a) or oxidizer Step (c). The Wacker catalyst mixture is an aqueous solution that contains, for example, palladium chloride, and Copper I and Copper II chloride. In this process alpha olefin is continuously added to this catalyst mixture in the reaction zone of Step (a).

The conditions in the reaction zone of Step (a) containing the reaction mixture are preferably between about 90 and 120° C. at a pressure between about 50 and 200 psig with between about 110° C. and 150 psig being most preferred.

Step (c) is an oxidation step that oxidizes the reduced catalyst stream so that it can be returned to the reaction zone in Step (a). The oxygen containing gas in the oxygenation step (c) is preferably air. The oxygenation conducted in Step (c) is preferably conducted at a temperature between about 190 and 120° C. at a pressure between about 50 and 200 psig, with about 110° C. and 150 psig being most preferred.

Once the catalyst stream that has been separated from the reaction mixture is oxidized in Step (c) it is returned to the reaction mixture in Step (a) in the reaction zone at a pH between about 0 and 2. It is important that this pH not go above 2 since it has been found that if the pH of the catalyst mixture goes much above this pH chlorination becomes unacceptably high. This pH is preferably between about 0.1 and 1 with about 0.5 being most preferred.

As illustrated in the following examples the process of the present invention significantly reduces the production of chlorinated byproducts as much as 93%. This is due, at least in part, to the lowered pH through the addition of strong acid such as hydrochloric or sulfuric acid to the catalyst in the reaction mixture. Further, a reduction in chlorinated byproducts was established in an inplant continuous process experiment to be as much as 40% using the Wacker catalyst containing about 0.1 to 2 weight percent sulfuric acid. The reduction in the chlorinated byproducts was manifested in the inplant process by reduction in hydrochloric acid makeup requirements.

This reduction in the production of chlorinated byproducts by the addition of strong acid is unexpected and in fact lowering the pH by the addition of strong acid was found to be detrimental to the rate of reaction. However, it was also found that the disadvantage of this reduction in the reaction rate is far outweighed by the reduction in the production of chlorinated byproducts, particularly when using sulfuric acid. The reaction rate can also be raised close to normal by lowering the chloride ion to copper ion ratio. The Cl/Cu ratio is preferably between about 1.5 and 2.1. More preferably between about 1.7 and 2.0 with about 1.8 being most preferred. Additionally, contrary to what was expected, the addition of sulfur to the Wacker catalyst in the form of sulfuric acid was not detrimental to the Wacker catalyst.

The following examples are set forth to illustrate the present invention but are not intended to limit the reasonable scope thereof.

EXAMPLES

GENERAL PROCEDURE FOR AUTOCLAVE EXPERIMENTS

A nitrogen purged 300 milliliter autoclave was charged with the designated catalyst, cooled in an ice-water bath, and further charged with acetaldehyde. The autoclave was heated to target temperature with slow stirring and then, with stirring discontinued, charged with either ethylene or air. Stirring was commenced at >2,300 rpm for the desired time and then stopped. The autoclave was plunged into an ice water bath and allowed to cool to room temperature. Vent gas and catalyst samples were analyzed for impurities content by gas chromatography.

EXAMPLE 1

Figure 1:
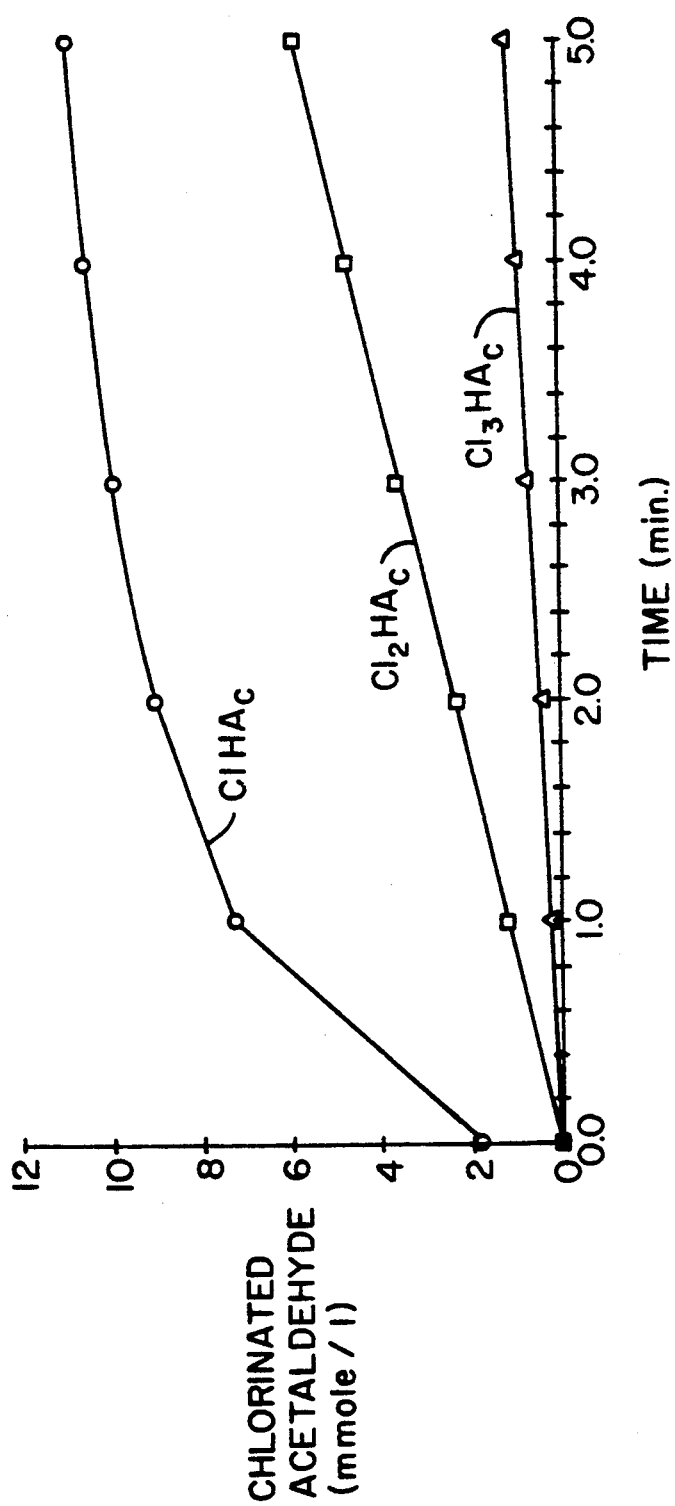
FIG. 1 illustrates the amounts of the three chlorinated acetaldehydes that are produced over time in the reaction without the addition of strong acid.
Figure 2:
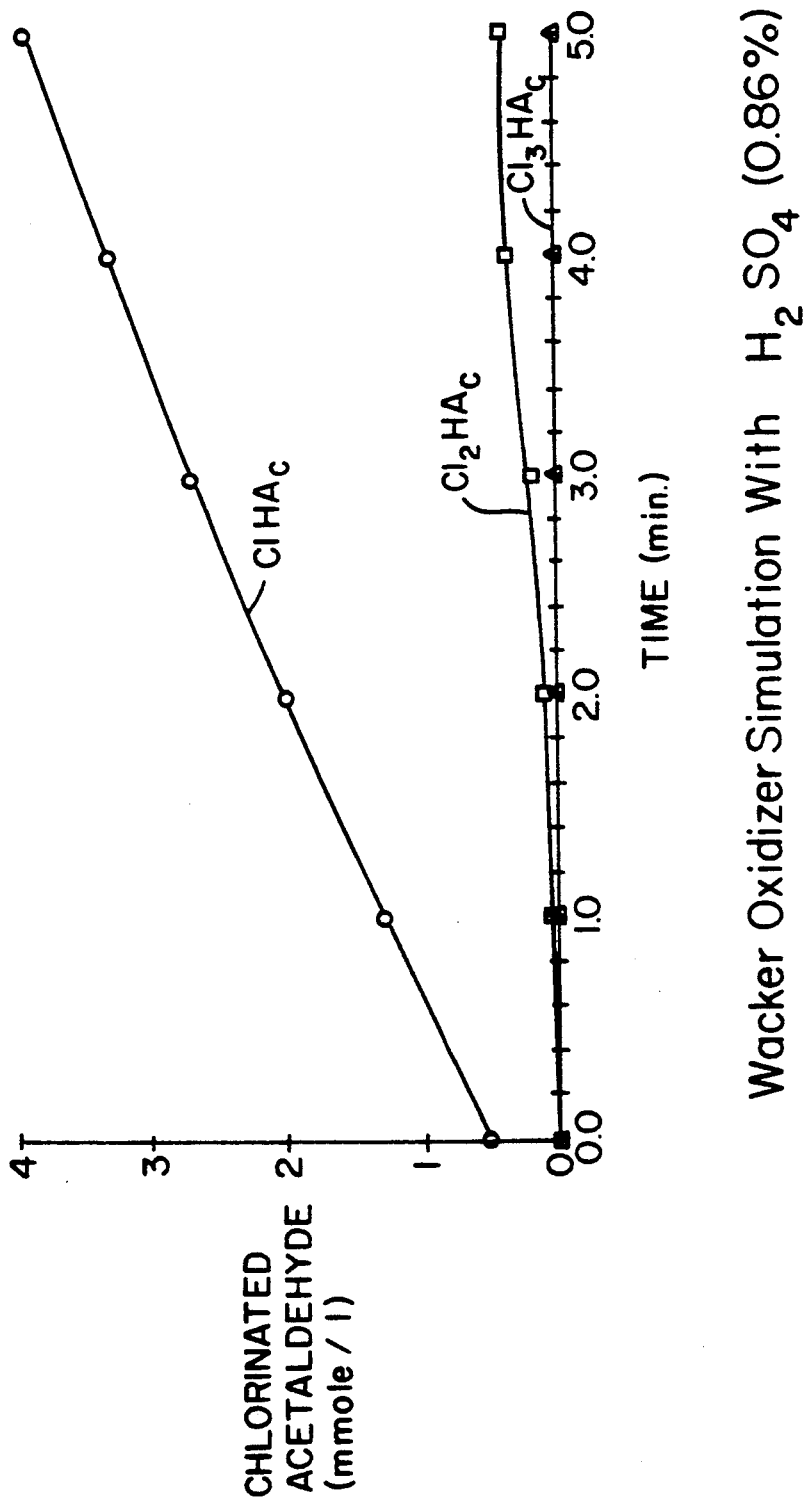

This example illustrates the effect of acid concentration on the production of chlorinated byproducts and autoclave experiments simulating Wacker Process oxidizer conditions. The catalyst consisted of palladium chloride, 10 millimole per liter; cuprous chloride, 459 millimole per liter cupric chloride, 891 millimole per liter; acetaldehyde, 236 millimole per liter; acetic acid, 10 millimole per liter; balance, water. Different amounts of sulfuric acid or HCl were added to this catalyst solution to evaluate the effect on chlorinated acetaldehyde production. The autoclave containing 150 milliliters of this catalyst solution was stirred at >2,300 rpm for 1 minute at 112° C. and 165 psia air. Stirring was discontinued and the autoclave allowed to sit at reaction temperature and pressure from 1 minute to 5 minutes. Catalyst samples withdrawn from the autoclave after 1 minute and 5 minute reaction times were analyzed for chloroacetaldehydes and other impurities by gas chromatography. Chlorinated acetaldehyde content in the samples were plotted as a function of time and the results are shown in FIGS. 1 (no sulfuric acid) and 2 (0.86 percent sulfuric acid). This data was generated for a number of cases and the results are listed in Table I and FIG. 3. These results indicate a 62 to 93 percent reduction in chlorination for sulfuric acid concentrations of 0.86 percent to 1.7 percent.

TABLE I

| | Acetaldehyde Oxidizer Simulation Chlorinated Aldehyde Analyses | | | |
|---|---|---|---|---|
| Expt. No. | 1 | 2 | 3 | 4 |
| Additive | None | HCl(0.6%) | H$_2$SO$_4$(0.86%) | H$_2$SO$_4$(1.7%) |
| Cl × HAc (total)* | 7.8 | 3 | 1.5 | 0.6 |
| HCl Reduction (%)** | 0 | 62 | 81 | 93 |

*Chlorinated acetaldehyde (Cl × HAc) produced expressed in milliequivalents of HCl.
**Percent reduction of HCl (Cl × HAc).

EXAMPLE 2

This example was run similar to Example 1 but was an inplant experiment with a 0.3 percent sulfuric acid concentration in the catalyst. This example illustrates the relationship between chlorinated acetaldehydes generated by the Wacker catalyst and sulfuric acid concentration in the catalyst. The results show reduced chlorination due to the addition of sulfuric acid to Wacker catalyst in an acetaldehyde plant process, evidenced by a 22 percent and 37 percent decrease in HCl usage, and are illustrated in Table II.

TABLE II

| Effect of Sulfuric Acid on HCl Consumption in the Acetaldehyde Wacker Process | | | |
|---|---|---|---|
| (%) Sulfuric Acid in Catalyst Solution | Acetaldehyde (lbs/Day) | HCl Usage (lbs/day) | (%) Decrease in HCl Consumption |
| 0 | 712,000 | 15,400 | 0 |
| 0.3 | 715,258 | 12,091 | 22 |
| 0 | 689,000 | 21,000 | 0 |
| 0.83 | 713,000 | 13,136 | 37 |

These two examples show the wide range of reduction in chlorination obtained by lowering the pH through the addition of acid to Wacker catalyst in the Wacker Process.

EXAMPLE 3

This example illustrates the effect of sulfuric acid concentration on reaction rate in autoclave experiments simulating Wacker Process reactor conditions. Thus, an autoclave containing 150 milliliters of the Wacker catalyst described in Example 1, except with a cuprous ion concentration of 12 percent instead of 34 percent, was stirred for 100 seconds at 2,300 rpm at 115° C. and 150 psia ethylene pressure. Ethylene consumption(pressure drop) or acetaldehyde production was monitored as a function of time and the results are tabulated in Table III. Lowering the chloride to copper ratio (Cl/Cu) from from 1.98 to 1.80 resulted in an increase in reaction rate from 2.7 to 4.9 millimoles ethylene per liter of catalyst per second and pH (0.7 to 1.8). The addition of sulfuric acid to the Cl/Cu 1.80 catalyst to give the same pH (0.7) as the Cl/Cu 1.98 catalyst gave a reaction rate of 4.4 millimole ethylene per liter catalyst per second. This demonstrates that the reaction rate for acetaldehyde production will be decreased by the addition of sulfuric acid to the catalyst unless the catalyst Cl/Cu ratio is reduced. The catalyst Cl/Cu ratio can be adjusted in plant operations by controlling the HCl make-up rate to the catalyst.

TABLE III

Acetaldehyde Reactor Simulation Experiments

| Experiment No. | Cl/Cu Ratio | $H_2SO_4$ (%) | pH | Rate (mmole ethylene/liter-catalyst/sec) |
|---|---|---|---|---|
| 1 | 1.98 | 0 | 0.7 | 2.7 |
| 2 | 1.8 | 0 | 1.8 | 4.9 |
| 3 | 1.8 | 0.3 | 0.7 | 4.4 |

The invention has been described in detail with particular reference to the preferred embodiments thereof; however, it should be understood that variations and modifications can be made without departing from the reasonable scope thereof.

We claim:

1. A process for the production of carbonyl compounds that produces low amounts of chlorinated by products comprising:
   (a) reacting an aqueous mixture of at least one alpha olefin, noble metal oxidation catalyst, cupric ions, chloride ions, and a strong acid selected from 0.05 to 5 wt. % sulfuric acid, 0.05 to 5 wt. % phosphoric acid, and 1 to 5 wt. % hydrochloric acid in a reaction zone under conditions to produce carbonyl compounds;
   (b) separating the mixture into a carbonyl compound stream, and a reduced catalyst stream;
   (c) introducing an oxygen containing gas into said reduced catalyst stream under oxidation conditions; and
   (d) returning the catalyst stream to said reaction zone at a pH between about 0 and 2.

2. The process according to claim 1 wherein the aqueous mixture of (a) contains sulfuric acid.

3. The process according to claim 2 wherein said aqueous mixture contains between about 0.1 and 3 weight percent sulfuric acid.

4. The process according to claim 1 wherein the noble metal oxidation catalyst contains a Group VIII noble metal.

5. The process according to claim 1 wherein said noble metal oxidation catalyst contains a metal salt selected from the group consisting essentially of salts of palladium, rhodium, ruthenium iridium, platinum, gold and mercury.

6. The process according to claim 5 wherein said noble metal oxidation catalyst is palladium chloride.

7. The process according to claim 1 wherein the alpha olefin is selected from alpha olefins having 2 to 5 carbon atoms.

8. The process according to claim 7 wherein the alpha olefin is ethylene and the carbonyl compound is acetaldehyde.

9. The process according to claim 1 wherein Steps (a) and (c) are conducted at a temperature between about 90 and 120° C. at a pressure between about 50 and 200 psig and said oxygen containing gas is air.

10. The process according to claim 9 wherein Steps (a) and (c) are conducted at about 110° C. at about 150 psig.

11. The process according to claim 1 wherein the catalyst contains between about 3 and 20 millimoles per liter of palladium chloride, between about 100 and 3,000 millimoles per liter of cupric chloride, and between about 10 and 1,000 millimoles per liter cuprous chloride.

12. The process according to claim 11 wherein the catalyst in Step (a) comprises about 10 millimoles per liter palladium chloride, about 1,000 millimoles per liter cupric chloride and about 300 millimoles per liter cuprous chloride.

13. A process for producing carbonyl compounds comprising:
   (a) reacting an aqueous mixture containing at least one C2 to C5 alpha olefin, palladium salt, cupric ions, chloride ions, and about 0.05 to 5 wt. % sulfuric acid in a reaction zone under conditions to produce carbonyl compounds;
   (b) separating the mixture into a carbonyl compound stream and a reduced catalyst stream;
   (c) oxidizing said reduced catalyst stream; and
   (d) returning the oxidized catalyst stream to said reaction zone at a pH between about 0 and 2.

14. A process for the production of carbonyl compounds that produces low amounts of chlorinated by products comprising:
   (a) reacting an aqueous mixture of at least one C2–C5 alpha olefin, noble metal oxidation catalyst, cupric ions, chloride ions, and a strong acid selected from 0.05 to 5 wt. % sulfuric acid, 0.05 to 5 wt. % phosphoric acid, and 1 to 5 wt. % hydrochloric acid in a reaction zone at a temperature between 90 and 120° C. at a pressure between 50 and 200 psig to produce the corresponding C2–C5 carbonyl compound;
   (b) separating the mixture into a carbonyl compound stream, and a reduced catalyst stream;
   (c) introducing an oxygen containing gas into said reduced catalyst stream under oxidation conditions; and
   (d) returning the catalyst stream to said reaction zone at a pH between about 0 to 2.

15. The process according to claim 14 wherein the alpha olefin is ethylene and the carbonyl compound is acetaldehyde.

* * * * *